US008523937B2

(12) United States Patent
Lindsay et al.

(10) Patent No.: US 8,523,937 B2
(45) Date of Patent: Sep. 3, 2013

(54) CONTROLLED DRUG DELIVERY USING A ZEIN LAYER MODIFIED WITH LEVULINIC ACID

(75) Inventors: Ashley P. Lindsay, Brownsburg, IN (US); Waleska Perez-Segarra, Kingsport, TN (US); Patrick H. Ruane, San Mateo, CA (US); Christine Casterline, Crown Point, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 843 days.

(21) Appl. No.: 12/273,926

(22) Filed: Nov. 19, 2008

(65) Prior Publication Data

US 2009/0258050 A1 Oct. 15, 2009

Related U.S. Application Data (60) Provisional application No. 60/989,263, filed on Nov. 20, 2007.

(51) Int. Cl.
*A61F 2/06* (2013.01)

(52) U.S. Cl.
USPC ..... 623/1.46; 623/1.11; 623/1.42; 106/161.1; 560/170

(58) Field of Classification Search
USPC ............ 623/1.11, 1.42, 1.46; 106/161.1; 560/170
See application file for complete search history.

(56) References Cited

U.S. PATENT DOCUMENTS

| 4,885,357 A | 12/1989 | Larkins et al. ............. 530/373 |
| 5,580,959 A | 12/1996 | Cook et al. |
| 5,591,227 A | 1/1997 | Dinh et al. ............... 623/1.22 |
| 5,624,411 A | 4/1997 | Tuch ...................... 604/265 |
| 5,776,184 A | 7/1998 | Tuch ...................... 623/1.11 |
| 5,865,814 A | 2/1999 | Tuch ...................... 623/1.15 |
| 6,545,097 B2 | 4/2003 | Pinchuk et al. |
| 6,620,617 B2 | 9/2003 | Mathiowitz et al. ......... 435/325 |
| 6,679,910 B1 | 1/2004 | Granada |
| 6,911,216 B1 | 6/2005 | Roth et al. ............... 424/489 |
| 2003/0118649 A1 | 6/2003 | Gao et al. ................ 424/471 |
| 2004/0126405 A1 | 7/2004 | Sahatjian et al. ........... 424/423 |
| 2004/0215336 A1 | 10/2004 | Udipi et al. .............. 623/1.42 |
| 2004/0234575 A1 | 11/2004 | Horres et al. ............. 424/426 |
| 2005/0042277 A1* | 2/2005 | Srinivas et al. ............ 424/452 |
| 2005/0060028 A1* | 3/2005 | Horres et al. ............. 623/1.38 |
| 2005/0149172 A1 | 7/2005 | Varma .................... 623/1.38 |
| 2005/0152949 A1 | 7/2005 | Hotchkiss et al. .......... 424/423 |
| 2005/0175668 A1 | 8/2005 | Boothman et al. .......... 424/423 |
| 2005/0176678 A1 | 8/2005 | Horres et al. ............. 514/54 |
| 2005/0238616 A1 | 10/2005 | Dang et al. ............... 424/78.17 |
| 2007/0207183 A1* | 9/2007 | Ruane et al. ............. 424/423 |

FOREIGN PATENT DOCUMENTS

| EP | 0 158 277 A2 | 10/1985 |
| EP | 0 447 297 A1 | 9/1991 |
| EP | 0 585 688 A2 | 9/1994 |

OTHER PUBLICATIONS

Wang, H.J.; Lin, Z.X.; Liu, X.M.; Sheng, S.Y.; and Wang, J.Y.; "Heparin-loaded zein microsphere film and hemocompatibility," *Journal of Controlled Release*, 105 (2005), 120-131.
Dong, Jian; Sun, Qingshen; and Wang, Jin-Ye; "Basic study of corn protein, zein, as a biomaterial in tissue engineering, surface morphology and biocompatibility," *Biomaterials*, 25 (2004), 4691-4697.
Liu, Xinming; Sun, Gingshen; Wang, Huajie; Zhang, Lei; and Wang, Jin-Ye: "Microspheres of corn protein, zein, for an ivermectin drug delivery system," *Biomaterials*, 26 (2005), 109-115.
Sung Chul Kim, et al., "In vivo evaluation of polymeric micellar paclitaxel formulation: toxicity and efficacy", Journal of Controlled Release, Elsevier Science B.V., 72 (2001) 191-202, 2001.
Sigmund Silber, M.D., F.A.C.C., Paclitaxel-Eluting Stents: Are They All Equal? An Analysis of Six Randomized Controlled Trials in De Novo Lesions of 3,319 Patients, Journal of Interventional Cardiology, vol. 16, No. 6, 2003.
Takanori Miyoski, "Preparation of ultrafine fibrous zein membranes via electrospinning", 2005, Society of Chemical Industry, Polym Int 54:1187-1190 (2005).
PCT International Search Report for PCT/US2008/083869, Feb. 4, 2010.
PCT Written Opinion for PCT/US2008/083869, Feb. 4, 2010.
J.W. Lawton, "Platicizers for Zein: Their Effects on Tensile Properties and Water Absorption for Zein Films", Cereal Chem., vol. 81, No. 1, 2004, pp. 1-5, abstract p. 1, right column: "Film preparations".
M.I. Beck, "Physico-chemical characterization of zein as a film coating polymer. A direct comparison with ethyl cellulose", International Journal of Pharmaceutics, vol. 141, 1996, pp. 137-150, XP002564991, p. 148.
Office Action dated Jan. 28, 2010 for U.S. Appl. No. 11/650,034.
Office Action dated Apr. 21, 2009 for U.S. Appl. No. 11/650,034.
Robert S. Schwartz, et al., "Drug-Eluting Stents in Preclinical Studies: Recommended Evaluation From a Consensus Group", *Circulation* 2002; 106; 1867-1873.

* cited by examiner

*Primary Examiner* — Ali Soroush (74) *Attorney, Agent, or Firm* — Brinks Hofer Gilson & Lione (57) ABSTRACT

The disclosure relates to medical devices coated with zein admixed with levulinic acid. The medical device may further include a therapeutic agent in contact with zein admixed with levulinic acid. Zein admixed with levulinic acid allows the therapeutic agent to be retained on the device during delivery and also controls the elution rate of the therapeutic agent following implantation. The disclosure further relates to methods of delivering a therapeutic agent on said medical devices as well as their use especially in the form of stents for prevention of restenosis.

20 Claims, 6 Drawing Sheets

CONTROLLED DRUG DELIVERY USING A ZEIN LAYER MODIFIED WITH LEVULINIC ACID

PRIORITY CLAIM

This application claims the benefit of provisional U.S. patent application Ser. No. 60/989,263, filed Nov. 20, 2007, which is incorporated herein by reference in its entirety.

TECHNICAL FIELD

The present disclosure relates to implantable medical devices and the controlled release of therapeutic agents therefrom. The disclosure relates particularly to the use of a zein layer admixed with levulinic acid to control the elution rate of at least one therapeutic agent. The disclosure further describes methods for the local administration of therapeutic agents to a target site.

BACKGROUND OF THE DISCLOSURE

Delivery of a therapeutic agent via an implantable device is desirable for a variety of applications. For example, therapeutic agents applied to an implantable device may treat or mitigate such undesirable conditions as restenosis, inflammation, tumor development, or thrombosis formation.

Procedures for mitigating such conditions may include implantation of a device comprising a therapeutic agent. For example, implantations of stents during angioplasty procedures have substantially advanced the treatment of occluded blood vessels. Occasionally, angioplasty may be followed by an abrupt closure of the vessel or by a more gradual closure of the vessel, commonly known as "restenosis." Acute closure may result from an elastic rebound of the vessel wall and/or by the deposition of blood platelets and fibrin along a damaged length of the newly opened blood vessel. Restenosis may result from the natural healing reaction to the injury to the vessel wall (known as intimal hyperplasia), which involves the migration and proliferation of medial smooth muscle cells that continues until the vessel is again occluded.

To prevent such vessel occlusion, stents have been implanted within a body vessel. However, restenosis may still occur over the length of the stent and/or past the ends of the stent where the inward forces of the stenosis are unopposed. To reduce this problem, one or more therapeutic agents may be administered to the patient. For example, a therapeutic agent may be locally administered through a catheter positioned within the body vessel near the stent, or by coating the stent with the therapeutic agent.

Desirably, a medical device coated with a therapeutic agent is adapted to expose tissue within the body to the therapeutic agent over a desired time interval, such as by releasing the therapeutic agent. Desirably, the therapeutic agent is released within the body at a reproducible and predictable fashion so as to optimize the benefit of the therapeutic agent to the patient over the desired period of time. Providing coated medical devices adapted to release a therapeutic agent at a desired rate over a period of time is one challenge in designing implantable medical devices. For example, a coated medical device may release a therapeutic agent at a greater rate than desired upon implantation, and subsequently release the therapeutic agent at a slower rate than desired at some time after implantation.

The design configuration of an implantable device can be adapted to control the release of therapeutic agent from the device. For example, a therapeutic agent can be included in the implantable medical device, such as an implantable frame comprising a porous biostable material optionally mixed with or coated on top of a therapeutic agent. Current Drug Eluting Stents (DES) may incorporate permanent biostable polymers into their coatings. For example, U.S. Patent Applications 2005/0176678 and 2005/0060028 describe polymeric bioabsorbable coatings including polylactic acid and polyglycolic acid. However, there is some concern that these permanent polymers may lead to late thrombosis. It has been shown that various bioabsorbable polymers may produce an excess tissue response (*Heart*. 1998 April; 79(4):319-23). Implanted polymer coatings have been associated with a significant inflammatory and exaggerated neointimal proliferative response, as well as enhanced thrombotic response (*Circulation*. 1996; 94(7):1494-5).

As a consequence, there has been interest in recent years in developing alternative coating configurations that do not require durable polymers, but include a bioabsorbable material. Naturally occurring bioabsorbable coatings with improved biocompatibility are desirable. One suitable naturally-derived material is corn-derived proteins called zeins that constitute most of the storage proteins of maize seed. During development of the kernel, zein accretions form in the peripheral regions of the lumen of the rough endoplasmin reticulum. These ultimately develop into cytoplasmic deposits called vesicular protein bodies ranging in size from 1 to 3 μm in diameter. At maturity, zein comprises more than half of all extractable proteins found in the maize endosperm. Human liver cells and mouse fibroblast cells have been shown to attach to and proliferate on zein, suggesting that zein may be biocompatible. J. Dong et al., "Basic study of corn protein, zein, as a biomaterial in tissue engineering, surface morphology and biocompatibility," Biomaterials 25, 4691-4697 (2004). Further, Wang et al. describe a cardiovascular device coating comprising zein microspheres and heparin. H-J. Wang et al., "Heparin-loaded zein microsphere film and hemocompatibility," *Journal of Controlled Release* 105, 120-131 (2005).

However, zein coatings may be dry and brittle. There is some concern this characteristic may lead to tearing and cracks appearing in a zein coating, especially when the zein coating is thin. Further, an implantable device may be subjected to mechanical straining (e.g., crimping, loading into a delivery device, sterilizing) that may introduce cracks and peeling in a zein coating on the device.

SUMMARY

In one aspect, a medical device comprising a frame and a coating is provided. The coating comprises zein admixed with levulinic acid. The coating may further comprise therapeutic agent.

In another aspect, a medical device comprising a frame and a coating is provided. The coating comprises at least two layers. The first layer comprises a therapeutic agent. The second layer comprises zein or modified zein admixed with levulinic acid, and the second layer at least partially covers the first layer.

In a further aspect, a medical device comprising a frame and a coating is provided. The coating comprises about 1:1 to about 1:20 weight ratio of a taxane therapeutic agent to zein or modified zein admixed with levulinic acid.

In operation, one can deliver a therapeutic agent to a patient in need thereof by introducing a medical device in accordance with the present disclosure, wherein the medical device comprises at least one therapeutic agent and zein admixed with levulinic acid with a ratio of about 1:1 to about 1:20 by weight of the at least one therapeutic agent to zein admixed with levulinic acid.

Other systems, methods, features and advantages will be, or will become, apparent to one with skill in the art upon examination of the following figures and detailed description. It is intended that all such additional systems, methods, features and advantages be included within this description, be within the scope of the disclosure, and be protected by the following claims.

BRIEF DESCRIPTION OF THE DRAWINGS

The medical device may be better understood with reference to the following drawings and description. The components in the figures are not necessarily to scale, emphasis instead being placed upon illustrating the principles of the disclosure. Moreover, in the figures, like referenced numerals designate corresponding parts throughout the different views.

DETAILED DESCRIPTION

The present disclosure provides for a medical device coated with zein admixed with levulinic acid ("zein/levulinic acid"). The medical device may be configured to release a therapeutic agent from the medical device where the coating further includes a therapeutic agent in contact with the layer of zein/levulinic acid. The rate of release of the therapeutic agent may be influenced by the composition and structure of the medical device. The medical device may optionally include one or more bioabsorbable materials, biostable materials, or any combination thereof. Desirably, the medical device comprises materials configured to provide for the release of one or more therapeutic agents within a body lumen according to a therapeutically effective release profile.

Unless otherwise defined, all technical and scientific terms used herein have the same meaning as commonly understood by one of ordinary skill in the art to which this disclosure pertains. In case of conflict, the present document, including definitions, will control. Preferred methods and materials are described below, although methods and materials similar or equivalent to those described herein can be used in the practice or testing of the present disclosure. All publications, patent applications, patents and other references mentioned herein are incorporated by reference in their entirety. The materials, methods, and examples disclosed herein are illustrative only and not intended to be limiting.

Definitions

As used herein, the term "body vessel" means any tube-shaped body passage lumen that conducts fluid, including but not limited to blood vessels such as those of the human vasculature system, esophageal, intestinal, billiary, urethral and ureteral passages.

The term "biocompatible" refers to a material that is substantially non-toxic in the in vivo environment of its intended use, and that is not substantially rejected by the patient's physiological system (i.e., is non-antigenic). This can be gauged by the ability of a material to pass the biocompatibility tests set forth in International Standards Organization (ISO) Standard No. 10993 and/or the U.S. Pharmacopeia (USP) 23 and/or the U.S. Food and Drug Administration (FDA) blue book memorandum No. G95-1, entitled "Use of International Standard ISO-10993, Biological Evaluation of Medical Devices Part 1: Evaluation and Testing." Typically, these tests measure a material's toxicity, infectivity, pyrogenicity, irritation potential, reactivity, hemolytic activity, carcinogenicity and/or immunogenicity. A biocompatible structure or material, when introduced into a majority of patients, will not cause a significantly adverse, long-lived or escalating biological reaction or response, and is distinguished from a mild, transient inflammation which typically accompanies surgery or implantation of foreign objects into a living organism. The term "hydrophobic" refers to material that tends not to interact with water. One way of observing hydrophobicity is to observe the contact angle formed between a water droplet or solvent and a substrate; the higher the contact angle the more hydrophobic the surface. Generally, if the contact angle of a liquid on a substrate is greater than 90° then the material is said to be hydrophobic.

The term "implantable" refers to an ability of a medical device to be positioned, for any duration of time, at a location within a body, such as within a body vessel. Furthermore, the terms "implantation" and "implanted" refer to the positioning, for any duration of time, of a medical device at a location within a body, such as within a body vessel.

The term "interconnecting surface" refers to the surface of a medical device connecting a medical device abluminal surface to a medical device luminal surface.

The phrase "controlled release" refers to an adjustment in the rate of release of a therapeutic agent from a medical device in a given environment. The rate of a controlled release of a therapeutic agent may be constant or vary with time. A controlled release may be characterized by a drug elution profile, which shows the measured rate at which the therapeutic agent is removed from a drug-coated device in a given solvent environment as a function of time.

The phrase "therapeutic agent" refers to any pharmaceutically active agent that results in an intended therapeutic effect on the body to treat or prevent conditions or diseases. Therapeutic agents include any suitable biologically active chemical compounds, biologically derived components such as cells, peptides, antibodies, and polynucleotides, and radiochemical therapeutic agents, such as radioisotopes.

An "anti-proliferative" agent/factor/drug indicates any protein, peptide, chemical or other molecule that acts to inhibit cell proliferative events. Examples of anti-proliferative agents include microtubule inhibitors such as vinblastine, vincristine, colchicine and paclitaxel, or other agents such as cisplatin.

The term "pharmaceutically acceptable," refers to those compounds of the present disclosure which are, within the scope of sound medical judgment, suitable for use in contact with the tissues of humans and lower mammals without undue toxicity, irritation, and allergic response, are commensurate with a reasonable benefit/risk ratio, and are effective for their intended use, as well as the zwitterionic forms, where possible, of the compounds of the disclosure.

The term "coating," unless otherwise indicated, refers generally to material attached to an implantable medical device prior to implantation. A coating can include material covering any portion of a medical device, and can include one or more coating layers. A coating can have a substantially constant or a varied thickness and composition. Coatings can be adhered to any portion of a medical device surface, including the luminal surface, the abluminal surface, or any portions or combinations thereof.

"Pharmaceutically acceptable salt" means those salts which are, within the scope of sound medical judgement, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharm Sciences, 66: 1-19 (1977), which is hereby incorporated by reference.

The term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than six carbon atoms. Examples of particular esters includes formates, acetates, propionates, butyates, acrylates and ethylsuccinates.

The term "pharmaceutically acceptable prodrug" refers to those prodrugs of the compounds of the present disclosure which are, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the disclosure. The term "prodrug" refers to compounds that are rapidly transformed in vivo to provide the parent compound having the above formula, for example by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

Zein

Zein may be obtained from any suitable source, but is preferably obtained from maize. Various methods and techniques exist for extracting zein from the maize endosperm. Laboratory preparation of zein, for example, involves extracting zein from maize endosperm with aqueous ethanol or isopropanol under mild conditions (such as an extraction temperature less than 10 degrees Celsius) with or without reducing agents. Commercial zein is typically extracted from corn gluten meal. For example, U.S. Pat. Nos. 3,535,305; 5,367,055; 5,342,923; and 5,510,463 disclose extraction of zein from corn gluten using aqueous-alcohol solutions.

The study of zein reveals an extreme variability at the genetic level and consequently a complex situation amongst the zein proteins. Native zein is actually a large, heterogeneous family of several groups of proteins that differ in molecular size, solubility, and charge. More than twenty different zein polypeptides have been estimated to exist. Analysis of zein extracts using high-performance liquid chromatography (HPLC), ion-exchange chromatography, gel exclusion chromatography, SDS-polyacrylamide gel electrophoresis (SDS-PAGE), isoelectric focusing (IEF), amino acid analysis, and DNA cloning techniques have led to a greatly improved understanding of zein proteins.

Amino acid composition analyses of zein disclose large amounts of leucine, alanine, glutamine, and phenylalanine; lysine and tryptophan are absent or present in very small amounts. The high proportion of non-polar amino acid residues and the exceptional lack of ionic groups are responsible for the highly hydrophobic nature of zein and for its unique solubility.

Zein protein bodies are composed of three structurally distinct types of proteins: $\alpha$-zein, $\gamma$-zein (which includes $\beta$-zein), and $\delta$-zein. These can be further differentiated into four classes ($\alpha$-, $\beta$-, $\gamma$-, and $\delta$-) on the basis of differences in solubility and sequence.

Zein extracted without reducing agents forms a large multigene family of polypeptides, termed $\alpha$-zein. Typically the most abundant faction of native zein, $\alpha$-Zeins contain about 40 N-terminal amino acids that precede a series of nine or ten repeated peptides of 20 amino acids. These repeats are predicted to be $\alpha$-helical and wind the protein into a rod-shaped molecule.

The other fractions of zein ($\beta$-, $\gamma$-, and $\delta$-zein) must be extracted using aqueous alcohols containing reducing agents to break disulfide bonds. For example, mercaptoethanol is used for laboratory extraction. $\beta$-, $\gamma$-, and $\delta$-zein show no sequence homology with $\alpha$-zein.

$\gamma$-Zein is soluble in both aqueous and alcoholic solvents with reducing conditions. Each of the $\gamma$-zeins has a unique N-terminal sequence. For example, in the 50 kDa $\gamma$-zein, this region is 136 amino acids long and it is very H is rich. The 27 kDa $\gamma$-zein protein has a series of eight tandem hexapeptide repeats that occur 11 amino acids after the N-terminus. The first eight amino acids of the 16 kDa $\gamma$-zein protein are identical to those of the 27 kDa $\gamma$-zein, but the 16 kDa $\gamma$-zein has three degenerate versions of Pro-rich repeat. $\gamma$-Zein typically comprises about 10 to 15% of total zein.

$\beta$-Zein, which is related to $\gamma$-zein, includes a methionine-rich polypeptide of 17 kDa and constitutes up to 10% of the total zein. Approximately the last 140 amino acids of the $\beta$- and $\gamma$-zeins are 85% identical. $\beta$-Zein has no repetitive peptides and appears to consist of mostly $\beta$-sheet and turn conformation.

$\delta$-Zein is a 10 kDa protein and is a minor fraction of zein. $\delta$-Zeins are the most hydrophobic of the group, contain no repetitive peptides, and are exceptionally rich in Met and Cys.

Zein has been considered as Generally Recognized as Safe (G.R.A.S.) by the Food and Drug Administration since 1985 (CAS Reg. No. 9010-66-6). The source or grade of zein is not limited, and any zein can be used in the present disclosure. For example, commercial zeins that may be used in the present disclosure include, but are not limited to, Sigma-Aldrich product number Z 3625; Wako Pure Chemical Industries product numbers 261-00015, 264-01281, and 260-01283; Spectrum Chemical product numbers Z1131 and ZE105; ScienceLab stock keeping unit SLZ1150; SJZ Chem-Pharma Company product name ZEIN (GLIDZIN); Arco Organics catalog numbers 17931-0000, 17931-1000, and 17931-5000; and Freeman Industries zein regular grade F4000, zein regular grade F4400, zein special grade F6000, zein G10 film coating solution, zein G20 film coating solution, aqua zein, and aqua zein natural. Desirably, the commercial zein in the present disclosure is product number Z 3625, zein from maize, obtained from Sigma-Aldrich, St. Louis, Mo.

The term "zein" as used herein includes native zein and modified zein. "Modified zein" includes zein proteins having an amino acid sequence which is not normally occurring, which behave similarly to authentic zeins, and which are soluble in alcohol. Amino acid substitutions, especially those which do not substantially modify the hydrophobicity, may be introduced. For example, amino acid substitution within the repeated sections, single amino acid substitution, as well as substitutions in the segments connecting the domains of repeated sequences may be employed. Also, insertions and substitutions can be made in both the COOH— terminus and the $NH_2$ terminus of the zein molecule.

Levulinic Acid

Levulinic acid is a keto acid that is commonly used as a food additive, among other things. Common alternative chemical names for levulinic acid include 4-Oxopentanoic acid, 4-Oxovaleric acid, gamma-Ketovaleric acid, 4-Ketovaleric acid, Laevulinic acid, β-Acetylpropionic acid, propionic acid, keto acid, 3-acetyl-, and 3-Acetopropionic acid. As used herein, "levulinic acid" refers to levulinic acid and any derivatives thereof. For example, levulinic acid derivatives include, but are not limited to, methyltetrahydrofuran and esters of levulinic acid.

Levulinic acid has been considered as Generally Recognized as Safe (G.R.A.S.) by the Food and Drug Administration (CAS Reg. No. 123-76-2). The source or grade of levulinic acid is not limited, and any levulinic acid may be used in the present disclosure.

Coating Configurations for Controlled Release

In one example, the therapeutic agent(s) included in the medical device is released locally into the adjacent or surrounding tissue in a controlled manner. This controlled release may involve an initial burst release of the therapeutic agent followed by a gradient or steady-state release of lesser amounts of therapeutic agent for an extended period of time, such as at least about one month. Desirably, the therapeutic agent is released over a period of at least about one to six months. More desirably, the therapeutic agent is released over a period of at least six months. To control the rate of release of a therapeutic agent from a medical device, a variety of coating configurations may be used.

In one example, the medical device includes a coating comprising at least one therapeutic agent and zein/levulinic acid. In another example, the medical device comprises a coating having two or more layers, each layer preferably being distinct layers having different chemical compositions, with one layer comprising at least one therapeutic agent and a second layer comprising zein/levulinic acid. Desirably, one layer consists essentially of a (or the at least one) therapeutic agent and a second layer consists essentially of zein/levulinic acid. In one example, the coating includes a layer comprising one or more therapeutic agent(s) that is substantially free of zein/levulinic acid and a second layer comprising zein/levulinic acid and being substantially free of the therapeutic agent. The coating includes at least one layer, and preferably two or more layers. For example, in one example, a layer of therapeutic agent is deposited on at least a portion of the surface of the medical device, or on a primer layer which is placed directly on the surface of the medical device, and a layer of zein/levulinic acid is deposited on at least a portion of the therapeutic agent layer. The zein/levulinic acid layer may serve as a barrier that slows the rate of release of the therapeutic agent by providing an additional layer through which the therapeutic agent must diffuse or by providing an additional layer that must degrade before releasing the therapeutic agent beneath it.

In another example, at least a portion of the abluminal surface of the medical device has a layer of admixed therapeutic agent, zein and levulinic acid. The zein/levulinic acid may function to increase the biocompatibility of the medical device, and the presence of a therapeutic agent on the abluminal surface of the device allows the release of the agent directly to the location in need of therapy.

The present disclosure also contemplates medical devices having various multiple layer coating configurations. For example, the device may be coated with alternating layers of therapeutic agent and zein/levulinic acid, alternating layers of therapeutic agent and a mixture of therapeutic agent and zein/levulinic acid, alternating layers of zein/levulinic acid and a mixture of therapeutic agent and zein/levulinic acid, or any other combination. Additionally, the coating configuration may contain multiple therapeutic agents (hydrophilic and/or hydrophobic), non-polymers (such as a vitamin), a porous biostable polymer, a bioabsorbable polymer, or any combination thereof.

The thickness of the coating affects the rate of release of the therapeutic agent from the medical device. For example, in a medical device having two layers, a base layer comprising therapeutic agent and an outer layer comprising zein/levulinic acid, increasing the thickness of the zein/levulinic acid layer(s) generally slows the rate of release of the therapeutic agent(s) from the therapeutic agent layer(s). If the thickness of the coating is too large, however, the durability of the coating may be decreased. Thick layers are subject to cracking, causing a spike in therapeutic agent elution. Desirably, the thickness of each therapeutic agent layer is between about 0.1 μm and about 10.0 μm. The thickness of each zein/levulinic acid layer is preferably between about 1.0 and 20.0 times thicker than an adjacent layer of therapeutic agent, between about 0.1 μm and about 200 μm; more preferably about 1.0 to about 5.0 times greater; and most preferably about 1.0 to about 3.0 times greater than the thickness of the therapeutic agent layer(s). More desirably, the thickness of each therapeutic agent layer is between about 0.5 μm and about 1.0 μm and the thickness of each layer of zein/levulinic acid is between about 1.0 μm and about 10.0 μm.

Desirably, the thickness of the entire coating (which may include one or more layers of therapeutic agent or one or more layers of zein/levulinic acid, one or more mixed layers containing both agent, zein, and levulinic acid) on the medical device is between about 0.2 μm and about 210 μm. The layers of therapeutic agent, the layers of zein/levulinic acid, and the mixed layers may be arranged in any configuration. More desirably, the thickness of the entire coating is between about 0.6 μm and about 15 μm. Even more desirably, the thickness of the entire coating is between about 0.6 μm and about 10 μm For example, for a stent having six layers (three layers of therapeutic agent and three layers of zein/levulinic acid, alternating), the total thickness of the coating layers would desirably be between about 1.5 μm to about 66.0 μm. Each of the layers can have the same or different thicknesses.

Figure 1:
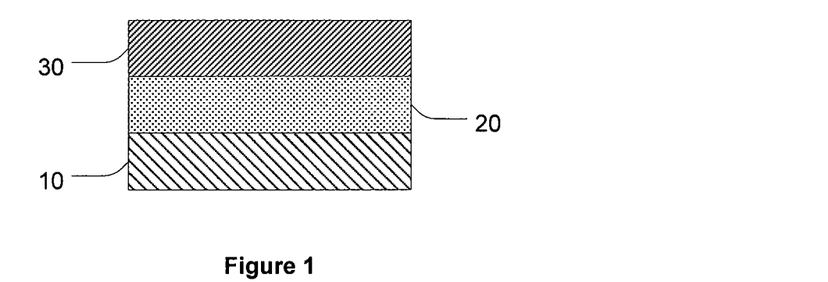
FIG. 1 is a schematic diagram showing a two-layer coating configuration according to one example.

FIG. 1 shows a cross-sectional view of the surface of a coated medical device comprising a first layer of paclitaxel therapeutic agent 20 deposited on an implantable frame 10, and a second layer of zein/levulinic acid 30 positioned over the first layer.

Figure 2:
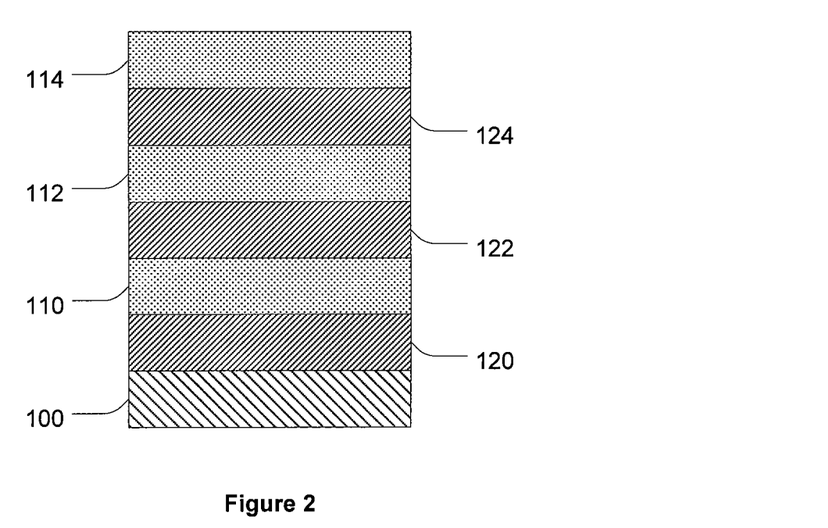
FIG. 2 is a schematic drawing showing a multilayer coating configuration according to one example.

FIG. 2 shows a cross-sectional view of the surface of a second coated medical device comprising six layers deposited on an implantable frame 100, where the first layer 120 contains zein/levulinic acid; the second layer 110 contains a therapeutic agent (desirably, paclitaxel); the third layer 122 contains zein/levulinic acid; the fourth layer 112 contains a therapeutic agent (desirably, paclitaxel); the fifth layer 124 contains zein/levulinic acid; and the sixth layer 114 contains a therapeutic agent (desirably, paclitaxel). In this example, the sixth layer 114 provides an initial "burst" of therapeutic agent, and then the zein/levulinic acid layers temporarily block the release or decrease the rate of release of the remaining layers of therapeutic agent.

The coating layer(s) may be deposited on the medical device in any suitable manner. For example, the coating may be deposited onto the medical device by spraying, dipping, pouring, pumping, brushing, wiping, ultrasonic deposition, vacuum deposition, vapor deposition, plasma deposition, electrostatic deposition, epitaxial growth, or any other method known to those skilled in the art.

Figure 3A:
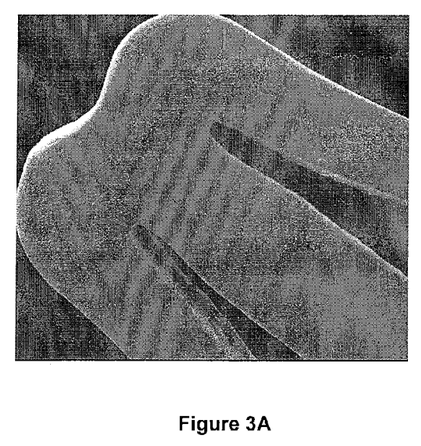
FIGS. 3A, 3B, 3C and 3D are SEM images of a ZILVER stent coated with paclitaxel and zein admixed with levulinic acid.
Figure 3B:
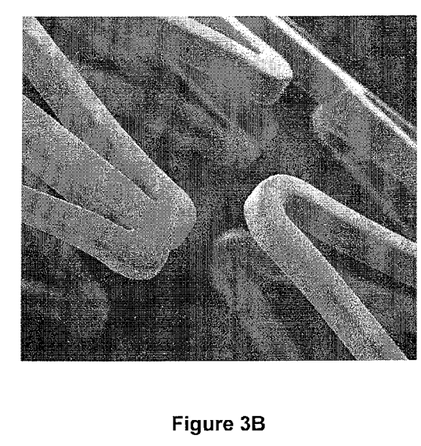
Figure 3C:
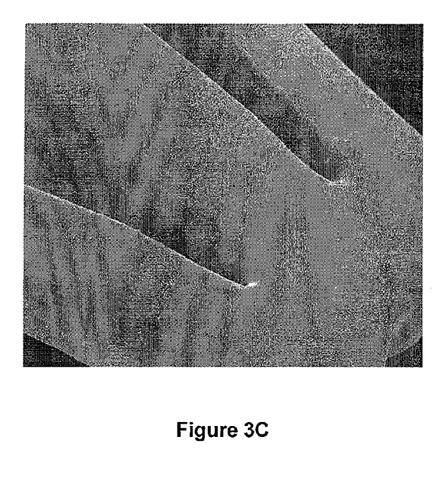
Figure 3D:
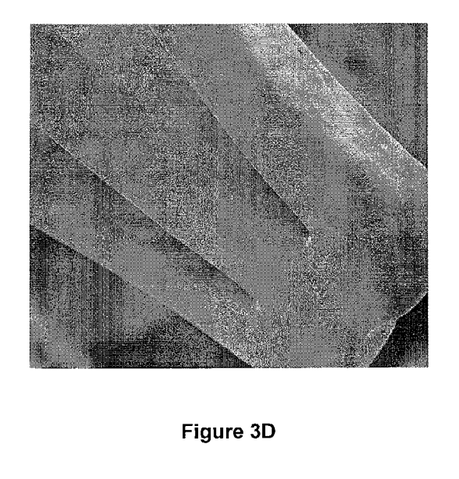
Figure 4:
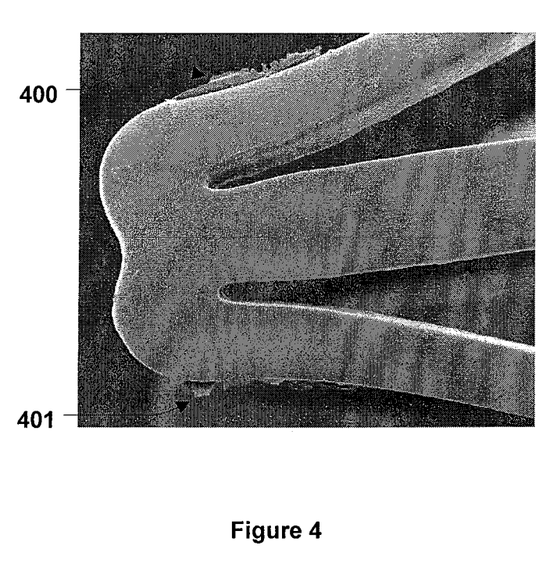
FIG. 4 is an SEM image of a paclitaxel-zein coated ZILVER stent.

FIGS. 3A-3D show SEM images of a ZILVER stent coated with a paclitaxel base layer and a zein/levulinic acid top layer, according to the coating configuration of FIG. 1. The SEM images of the ZILVER stent coated with paclitaxel and zein/levulinic acid are taken at magnification levels of 400× (FIG. 3A), 140× (FIG. 3B), 500× (FIG. 3C), and 400× (FIG. 3D). FIG. 4 is an SEM image of a paclitaxel-zein coated ZILVER stent. The zein layer of the stent is not admixed with levulinic acid. The zein coating is cracked and delaminating 400, 401 from the stent as a result of the dry and brittle nature of zein before it is modified with levulinic acid. This affects the elution rate of the therapeutic agent in a less controllable fashion. Conversely, the paclitaxel-zein/levulinic acid coated stent of FIGS. 3A-3D do not exhibit any dry, brittle regions or delamination. The levulinic acid has added significant elasticity to the coating so that it can accommodate deformations, for example deformations related to crimping and loading.

The stent of FIGS. 3A-3D was mounted on a mandrel assembly positioned in the lumen of the stent, thereby masking the lumen of the stent and preventing the lumen from being coated. Preferably, the therapeutic agent is applied by spraying a solution of a volatile solvent and about 0.5 to about 5.0 mM concentration of the therapeutic agent. For a paclitaxel therapeutic agent, a 0.6-4.0 mM solution (more preferably, about 0.6-3.0 mM) of paclitaxel in ethanol is preferably sprayed onto the abluminal surface of the stent. In the coatings shown in FIGS. 3A-3D, the abluminal surface and interconnecting surfaces of the stent were coated with a 2.4 mM ethanolic paclitaxel solution using a pressure spray gun and a 2 g/L zein/levulinic acid methanolic solution was applied to the paclitaxel using an ultrasonic nozzle. The loaded stent was subsequently crimped to 5.5 french and sterilized with ethylene oxide.

In other examples, each coating layer may also be separately applied using an ultrasonic nozzle spray coating technique employing ultrasound to atomize the spray solution. A solution of about 1-5 g/L of zein in a suitable solvent such as methanol admixed with about 1-3 drops of levulinic acid per 10 mL methanolic zein solution can be applied using an ultrasonic nozzle. Ultrasonic nozzles can be configured such that excitation of the piezoelectric crystals creates a transverse standing wave along the length of the nozzle. The ultrasonic energy originating from the crystals located in the large diameter of the nozzle body undergoes a step transition and amplification as the standing wave as it traverses the length of the nozzle. The ultrasonic nozzle can be designed so that a nodal plane is located between the crystals. For ultrasonic energy to be effective for atomization, the atomizing surface (nozzle tip) is preferably located at an anti-node, where the vibration amplitude is greatest. To accomplish this, the nozzle's length is preferably a multiple of a half-wavelength. Since wavelength is dependent upon operating frequency, nozzle dimensions can be related to operational frequency. In general, high frequency nozzles are smaller, create smaller drops, and consequently have smaller maximum flow capacity than nozzles that operate at lower frequencies. The ultrasonic nozzle can be operated at any suitable frequency, including 24 kHz, 35 kHz, 48 kHz, 60 kHz, 120 kHz or higher.

Preferably, a frequency of 60-120 kHz or higher is used to atomize the solution of the bioabsorbable elastomer to the greatest possible extent so as to promote the formation of a smooth, uniform coating. Power can be controlled by adjusting the output level on the power supply. The nozzle power can be set at any suitable level, but is preferably about 0.9-1.2 W and more preferably about 1.0-1.1 W. The nozzle body can be fabricated from any suitable material, including titanium because of its good acoustical properties, high tensile strength, and excellent corrosion resistance. Liquid introduced onto the atomizing surface through a large, non-clogging feed tube running the length of the nozzle absorbs some of the vibrational energy, setting up wave motion in the liquid on the surface. For the liquid to atomize, the vibrational amplitude of the atomizing surface can be maintained within a band of input power to produce the nozzle's characteristic fine, low velocity mist. Since the atomization mechanism relies only on liquid being introduced onto the atomizing surface, the rate at which liquid is atomized depends largely on the rate at which it is delivered to the surface. Therefore, an ultrasonic nozzle can have a wide flow rate range. The maximum flow rate and median drop diameter corresponding to particular nozzle designs can be selected as design parameters by one skilled in the art. Preferably, the flow rate is between about 0.01-2.00 mL/min, more preferably between about 0.05-1.00 and most preferably between about 0.05-0.10 mL/min. The ultrasonic nozzle is preferably rastered over the surface of the stent with a translational coating velocity of about 0.01-0.5 inches/second, more preferably about 0.02-0.1 in/sec and most preferably about 0.02-0.08 inches/sec. The stent is preferably rotated during the coating process, for example at about 30-150 rpm, more preferably at about 40-110 rpm and most preferably at about 90-110 rpm. The spray may be ejected from the nozzle using a suitable process gas, such as nitrogen, at a pressure that provides a desired rate of coating. The process gas is preferably nitrogen at about 0.1-2.5 psi, more preferably about 0.4-1.5 psi and most preferably about 0.5-1.0 psi. Preferred coating parameters for USD using a Sono-tek Model 8700-60 ultrasonic nozzle are provided in Table 1 below:

TABLE 1

| Ultrasonic Spray Deposition Parameters for Sono-tek Model 8700-60 | | | | | |
|---|---|---|---|---|---|
| Flow rate (mL/min) | Coating velocity (in/sec) | Rotation Speed (rpm) | Nozzle Power (watts) | Process Gas (psi) | Distance (mm) |
| 0.01-2 | 0.01-0.5 | 30-150 | 0.9-1.2 | 0.1-2.5 | 1-25 |

Optionally, the medical device may include a layer(s) in which the therapeutic agent is contained within the medical device itself. The medical device may have holes, wells, slots, grooves, or the like for containing the therapeutic agent or zein/levulinic acid (see, e.g., co-pending U.S. application Ser. No. 10/870,079, incorporated herein by reference). Alternatively, the therapeutic agent and/or zein/levulinic acid may be incorporated into a biodegradable structural material that releases the agent before or as the device degrades, or the therapeutic agent and/or zein/levulinic acid may be incorporated into or placed on the medical device in any other known manner. A medical device containing a therapeutic agent within the device itself may also have deposited on the device therapeutic layer, a zein/levulinic acid layer, a layer containing both therapeutic agent and zein/levulinic acid, or any combination of the foregoing.

The zein/levulinic acid is preferably applied to the medical device as a solution in a suitable solvent. The zein/levulinic acid solution preferably contains zein/levulinic acid and methanol, without ethanol or a therapeutic agent. The zein/levulinic acid solution is preferably sprayed onto the surface of a medical device, or onto the surface of a therapeutic agent coating on the medical device, in a manner permitting the solvent to evaporate to leave the zein/levulinic acid adhered to the surface of the medical device. Most preferably, the zein/levulinic acid solution is sprayed from an ultrasonic nozzle onto a medical device, or onto a therapeutic agent coated on a medical device.

In one example, a method of coating an implantable medical device to form a drug delivery system is provided. The method may include one or more of the following steps:

(a) providing an implantable medical device having a surface;

(b) depositing a first layer consisting essentially of a therapeutic agent on the surface of the medical device by the steps of: applying to the surface a first solution comprising a first solvent and the therapeutic agent dispersed in the first solvent (preferably, the first solution does not contain a polymer); evaporating the first solvent to form the first coating layer consisting essentially of the therapeutic agent on the surface; repeating the application and evaporation steps until the first layer contains between about 0.05 and 2.00 µg (preferably, 0.05 and 1.00 µg) of the therapeutic agent per $mm^2$ of the coated surface; and (c) depositing a second layer comprising zein/levulinic acid over the first coating layer on the medical device to form a coated medical device by the steps of: applying to the first layer a second solution comprising a second solvent and zein/levulinic acid dispersed in the second solvent;

(d) evaporating the second solvent to form at least a portion of the second coating layer; and (e) repeating the application and evaporation steps until the weight or thickness of the zein/levulinic acid in the second layer is between 1 and 20 times greater than the weight or thickness of the therapeutic agent in the first layer.

In one aspect, the coating includes a first layer consisting essentially of, or characterized by, a desired amount of the therapeutic agent, the first layer being substantially free of zein/levulinic acid. The first layer is desirably formed by spraying a first solution of the therapeutic agent in a volatile solvent onto the surface of a medical device. The first solution is preferably formed by dissolving a taxane therapeutic agent in ethanol. The coating preferably further includes a second layer consisting essentially of, or characterized by, a desired amount of zein/levulinic acid, the second layer being substantially free of the therapeutic agent in the first layer. The first layer is preferably positioned between the second layer and a surface of the medical device. The second layer may include, or consist essentially of, zein/levulinic acid that has not been contacted with a proteolytic enzyme such as pepsin. The second layer is desirably formed by spraying a second solution of the zein/levulinic acid in a volatile solvent onto the surface of a medical device, or onto the therapeutic agent coated by spraying the first solution onto the medical device. The second solution is preferably formed by dissolving zein/levulinic acid in methanol, and preferably does not include the therapeutic agent in the first solution. More preferably, the first solution consists of paclitaxel and ethanol and the second solution consists of zein/levulinic acid and methanol. Other examples provide coatings comprising three or more layers that include a layer comprising zein and a layer comprising a therapeutic agent. Preferably, multi-layer coatings are formed by spray coating two or more solutions onto the medical device, or onto previous coating layers on the medical device. The solutions may include one or more solvents that may be the same or different from one another. Preferably, the solutions include at least one volatile solvent that evaporates under the spraying conditions, and either zein or one or more therapeutic agents.

Therapeutic Agents

Desirably, an implantable medical device comprises a therapeutically effective amount of one or more therapeutic agents in pure form or in derivative form. Preferably, the derivative form is a pharmaceutically acceptable salt, ester or prodrug form. Alternatively, a medical device may be implanted in combination with the administration of a therapeutic agent from a catheter positioned within the body near the medical device, before, during or after implantation of the device.

Alternatively, a medical device may be implanted in combination with the administration of a therapeutic agent from a catheter positioned within the body near the medical device, before, during or after implantation of the device.

Therapeutic agents that may be used in the present disclosure include, but are not limited to, pharmaceutically acceptable compositions containing any of the therapeutic agents or classes of therapeutic agents listed herein, as well as any salts and/or pharmaceutically acceptable formulations thereof. Table 2 below provides a non-exclusive list of classes of therapeutic agents and some corresponding exemplary active ingredients.

TABLE 2

| Therapeutic Agent Class | Exemplary Therapeutic Agent Active Ingredients |
|---|---|
| Adrenergic agonist | Adrafinil |
|  | Isometheptene |
|  | Ephedrine (all forms) |
| Adrenergic antagonist | Monatepil maleate |
|  | Naftopidil |
|  | Carvedilol |
|  | Moxisylyte HCl |
| Adrenergic - Vasoconstrictor/ | Oxymetazoline HCl |
| Nasal decongestant | Norfenefrine HCl |
|  | Bretylium Tosylate |
| Adrenocorticotropic hormone | Corticotropin |
| Analgesic | Bezitramide |
|  | Bupivacaine |
|  | Acetylsalicysalicylic acid |
|  | Propanidid |
|  | Lidocaine |
|  | Pseudophedrine HCl |
|  | Acetominophen |
|  | Chlorpheniramine Maleate |
| Anesthetics | Dyclonine HCl |
|  | Hydroxydione Sodium |
|  | Acetamidoeugenol |
| Anthelmintics | Niclosamide |
|  | Thymyl N-Isoamylcarbamate |
|  | Oxamniquine |
|  | Nitroxynil N-ethylglucamine |
|  | Anthiolimine |
|  | 8-Hydroxyquinoline Sulfate |
| Anti-inflammatory | Bendazac |
|  | Bufexamac |
|  | Desoximetasone |
|  | Amiprilose HCl |
|  | Balsalazide Disodium Salt |
|  | Benzydamine HCl |
| Antiallergic | Fluticasone propionate |
|  | Pemirolast Potassium salt |
|  | Cromolyn Disodium salt |
|  | Nedocromil Disodium salt |
| Antiamebic | Cephaeline |
|  | Phanquinone |
|  | Thiocarbarsone |

TABLE 2-continued

| Therapeutic Agent Class | Exemplary Therapeutic Agent Active Ingredients |
|---|---|
| Antianemic | Folarin |
|  | Calcium folinate |
| Antianginal | Verapamil |
|  | Molsidomine |
|  | Isosorbide Dinitrate |
|  | Acebutolol HCl |
|  | Bufetolol HCl |
|  | Timolol Hydrogen maleate salt |
| Antiarrhythmics | Quinidine |
|  | Lidocaine |
|  | Capobenic Acid |
|  | Encainide HCl |
|  | Bretylium Tosylate |
|  | Butobendine Dichloride |
| Antiarthritics | Azathioprine |
|  | Calcium 3-aurothio-2-propanol-1-sulfate |
|  | Glucosamine Beta Form |
|  | Actarit |
| Antiasthmatics/Leukotriene antagonist | Cromalyn Disodium |
|  | Halamid |
|  | Montelukast Monosodium salt |
| Antibacterial | Cefoxitin Sodium salt |
|  | Lincolcina |
|  | Colisitin sulfate |
| Antibiotics | Gentamicin |
|  | Erythromycin |
|  | Azithromycin |
| Anticoagulants | Heparin sodium salt |
|  | Dextran Sulfate Sodium |
| Anticonvulsants | Paramethadione |
|  | Phenobarbital sodium salt |
|  | Levetiracetam |
| Antidepressants | Fluoxetine HCl |
|  | Paroxetine |
|  | Nortiptyline HCl |
| Antidiabetic | Acarbose |
|  | Novorapid |
|  | Diabex |
| Antiemetics | Chlorpromazine HCl |
|  | Cyclizine HCl |
|  | Dimenhydrinate |
| Antiglaucoma agents | Dorzolamide HCl |
|  | Epinepherine (all forms) |
|  | Dipivefrin HCl |
| Antihistamines | Histapyrrodine HCl |
| Antihyperlipoproteinemic | Lovastatin |
|  | Pantethine |
| Antihypertensives | Atenolol |
|  | Guanabenz Monoacetate |
|  | Hydroflumethiazide |
| Antihyperthyroid | Propylthiouracil |
|  | Iodine |
| Antihypotensive | Cortensor |
|  | Pholedrine Sulfate |
|  | Norepinephrine HCl |
| Antimalarials | Cinchonidine |
|  | Cinchonine |
|  | Pyrimethamine |
|  | Amodiaquin 2 HCl dihydrate |
|  | Bebeerine HCl |
|  | Chloroquine Diphosphate |
| Antimigraine agents | Dihydroergotamine |
|  | Ergotamine |
|  | Eletriptan Hydrobromide |
|  | Valproic Acid Sodium salt |
|  | Dihydroergotamine mesylate |
| Antineoplastic | 9-Aminocamptothecin |
|  | Carboquone |
|  | Benzodepa |
|  | Bleomycins |
|  | Capecitabine |
|  | Doxorubicin HCl |
| Antiparkinsons agents | Methixene |
|  | Terguride |
|  | Amantadine HCl |
|  | Ethylbenzhydramine HCl |
|  | Scopolamine N-Oxide Hydrobromide |
| Antiperistaltic; antidiarrheal | Bismuth Subcarbonate |
|  | Bismuth Subsalicylate |
|  | Mebiquine |
|  | Diphenoxylate HCl |
| Antiprotozoal | Fumagillin |
|  | Melarsoprol |
|  | Nitazoxanide |
|  | Aeropent |
|  | Pentamideine Isethionate |
|  | Oxophenarsine HCl |
| Antipsycotics | Chlorprothixene |
|  | Cyamemazine |
|  | Thioridazine |
|  | Haloperidol HCl |
|  | Triflupromazine HCl |
|  | Trifluperidol HCl |
| Antipyretics | Dipyrocetyl |
|  | Naproxen |
|  | Tetrandrine |
|  | Imidazole Salicylate |
|  | Lysine Acetylsalicylate |
|  | Magnesium Acetylsalicylate |
| Antirheumatic | Auranofin |
|  | Azathioprine |
|  | Myoral |
|  | Penicillamine HCl |
|  | Chloroquine Diphosphate |
|  | Hydroxychloroquine Sulfate |
| Antispasmodic | Ethaverine |
|  | Octaverine |
|  | Rociverine |
|  | Ethaverine HCl |
|  | Fenpiverinium Bromide |
|  | Leiopyrrole HCl |
| Antithrombotic | Plafibride |
|  | Triflusal |
|  | Sulfinpyrazone |
|  | Ticlopidine HCl |
| Antitussives | Anethole |
|  | Hydrocodone |
|  | Oxeladin |
|  | Amicihone HCl |
|  | Butethamate Citrate |
|  | Carbetapentane Citrate |
| Antiulcer agents | Polaprezinc |
|  | Lafutidine |
|  | Plaunotol |
|  | Ranitidine HCl |
|  | Pirenzepine 2 HCl |
|  | Misoprostol |
| Antiviral agents | Nelfinavir |
|  | Atazanavir |
|  | Amantadine |
|  | Acyclovir |
|  | Rimantadine HCl |
|  | Epivar |
|  | Crixivan |
| Anxiolytics | Alprazolam |
|  | Cloxazolam |
|  | Oxazolam |
|  | Flesinoxan HCl |
|  | Chlordiazepoxide HCl |
|  | Clorazepic Acid Dipotassium salt |
| Bronchodialtor | Epinephrine |
|  | Theobromine |
|  | Dypylline |
|  | Eprozinol 2HCl |
|  | Etafedrine |
| Cardiotonics | Cymarin |
|  | Oleandrin |
|  | Docarpamine |
|  | Digitalin |
|  | Dopamine HCl |
|  | Heptaminol HCl |

TABLE 2-continued

| Therapeutic Agent Class | Exemplary Therapeutic Agent Active Ingredients |
|---|---|
| Cholinergic | Eseridine |
| | Physostigmine |
| | Methacholine Chloride |
| | Edrophonium chloride |
| | Juvastigmin |
| Cholinergic antagonist | Pehencarbamide HCl |
| | Glycopyrrolate |
| | Hyoscyamine Sulfate dihydrate |
| Cognition enhancers/Nootropic | Idebenone |
| | Tacrine HCl |
| | Aceglutamide Aluminum Complex |
| | Acetylcarnitine L HCl |
| Decongestants | Propylhexedrine dl-Form |
| | Pseudoephedrine |
| | Tuaminoheptane |
| | Cyclopentamine HCl |
| | Fenoxazoline HCl |
| | Naphazoline HCl |
| Diagnostic aid | Disofenin |
| | Ethiodized Oil |
| | Fluorescein |
| | Diatrizoate sodium |
| | Meglumine Diatrizoate |
| Diuretics | Bendroflumethiazide |
| | Fenquizone |
| | Mercurous Chloride |
| | Amiloride HCl 2•$H_2O$ |
| | Manicol |
| | Urea |
| Enzyme inhibitor (proteinase) | Gabexate Methanesulfonate |
| Fungicides | Candicidin |
| | Filipin |
| | Lucensomycin |
| | Amphotericin B |
| | Caspofungin Acetate |
| | Viridin |
| Gonad stimulating principle | Clomiphene Citrate |
| | Chorionic gonadotropin |
| | Humegon |
| | Luteinizing hormone (LH) |
| Hemorrheologic agent | Poloxamer 331 |
| | Azupentat |
| Hemostatic | Hydrastine |
| | Alginic Acid |
| | Batroxobin |
| | 6-Aminohexanoic acid |
| | Factor IX |
| | Carbazochrome Salicylate |
| Hypolimpernic agents | Clofibric Acid Magnesium salt |
| | Dextran Sulfate Sodium |
| | Meglutol |
| Immunosuppresants | Azathioprine |
| | 6-Mercaptopurine |
| | Prograf |
| | Brequinar Sodium salt |
| | Gusperimus 3 HCl |
| | Mizoribine |
| | Rapamycin and analogs thereof |
| Mydriatic; antispasmodic | Epinephrine |
| | Yohimbine |
| | Aminopentamide dl-Form |
| | Atropine Methylnitrate |
| | Atropine Sulfatemonohydrate |
| | Hydroxyamphetamine (I, HCl, HBr) |
| Neuromuscular blocking agent/ Muscle relaxants (skeletal) | Phenprobamate |
| | Chlorzoxazone |
| | Mephenoxalone |
| | Mioblock |
| | Doxacurium Chloride |
| | Pancuronium bromide |
| Oxotocic | Ergonovine Tartrate hydrate |
| | Methylergonovine |
| | Prostaglandin $F_{2\alpha}$ |
| | Intertocine-S |

TABLE 2-continued

| Therapeutic Agent Class | Exemplary Therapeutic Agent Active Ingredients |
|---|---|
| | Ergonovine Maleate |
| | Prostoglandin $F_{2\alpha}$Tromethamine salt |
| Radioprotective agent | Amifostine $3H_2O$ |
| Sedative/Hypnotic | Haloxazolam |
| | Butalbital |
| | Butethal |
| | Pentaerythritol Chloral |
| | Diethylbromoacetamide |
| | Barbital Sodium salt |
| Serenic | Eltoprazine |
| Tocolytic agents | Albuterol Sulfate |
| | Terbutaline sulfate |
| Treatment of cystic fibrosis | Uridine 5'-Triphosphate Trisodium dihydrate salt |
| Vasoconstrictor | Nordefrin (−) Form |
| | Propylhexedrine dl-form |
| | Nordefrin HCl |
| Vasodilators | Nylidrin HCl |
| | Papaverine |
| | Erythrityl Tetranitrate |
| | Pentoxifylline |
| | Diazenium diolates |
| | Citicoline |
| | Hexestrol Bis(diethylaminoethyl ether) 2HCl |
| Vitamins | α-Carotene |
| | β-Carotene |
| | Vitamin $D_3$ |
| | Pantothenic Acid sodium salt |

Other desirable therapeutic agents include, but are not limited to, the following: (a) anti-inflammatory/immunomodulators such as dexamethasone, m-prednisolone, interferon g-1b, leflunomide, sirolimus, tacrolimus, everolimus, pimecrolimus, biolimus (such as Biolimus A7 or A9) mycophenolic acid, mizoribine, cyclosporine, tranilast, and viral proteins; (b) antiproliferatives such as paclitaxel or other taxane derivatives (such as QP-2), actinomycin, methothrexate, angiopeptin, vincristine, mitomycine, statins, C MYC antisense, ABT-578, RestenASE, Resten-NG, 2-chloro-deoxyadenosine, and PCNA ribozyme; (c) migration inhibitors/ECM-modulators such as batimastat, prolyl hydroxylase inhibitors, halofuginone, C proteinase inhibitors, and probucol; and (d) agents that promote healing and re-endotheliazation such as BCP671, VEGF, estradiols (such as 17-beta estradiol (estrogen)), NO donors, EPC antibodies, biorest, ECs, CD-34 antibodies, and advanced coatings.

A preferred class of therapeutic agents which may be employed in the present disclosure are the family of so-called taxanes. These comprise molecules containing the core fused ring chemical structure shaded in structure (1) below, with four fused rings ("core taxane structure," shaded in structure (1)), with several substituents.

(1)

In another embodiment, the therapeutic agent can be a taxane analog or derivative characterized by variation of the paclitaxel structure (1). Taxanes in general, and paclitaxel is particular, is considered to function as a cell cycle inhibitor by acting as an anti-microtubule agent, and more specifically as a stabilizer. Preferred taxane analogs and derivatives core vary the substituents attached to the core taxane structure.

Within some preferred embodiments of the disclosure, the therapeutic agent is a taxane cell cycle inhibitor, such as paclitaxel, a paclitaxel analogue or paclitaxel derivative compound. Paclitaxel is a bioactive compound which disrupts mitosis (M-phase) by binding to tubulin to form abnormal mitotic spindles or an analogue or derivative thereof. Briefly, paclitaxel is a highly derivatized diterpenoid (Wani et al., *J. Am. Chem. Soc.* 93: 2325, 1971) which has been obtained from the harvested and dried bark of *Taxus brevifolia* (Pacific Yew) and Taxomyces Andreanae and Endophytic Fungus of the Pacific Yew (Stierle et al., *Science* 60: 214-216, 1993).

In one embodiment, the therapeutic agent is a taxane analog or derivative including the core taxane structure (1) and the methyl 3-(benzamido)-2-hydroxy-3-phenylpropanoate moiety (shown in structure (2) below) at the 13-carbon position ("C13") of the core taxane structure (outlined with a dashed line in structure (1)).

(2)

methyl 3-(benzamido)-2-hydroxy-3-phenylpropanoate

It is believed that structure (2) at the 13-carbon position of the core taxane structure plays a role in the biological activity of the molecule as a cell cycle inhibitor. Examples of therapeutic agents having structure (2) include paclitaxel (Merck Index entry 7117), docetaxol (TAXOTERE, Merck Index entry 3458), and 3'-desphenyl-3'-(4-ntirophenyl)-N— dibenzoyl-N-(t-butoxycarbonyl)-10-deacetyltaxol.

A therapeutic agent composition comprising a taxane compound can include formulations, prodrugs, analogues and derivatives of paclitaxel such as, for example, TAXOL (Bristol Myers Squibb, New York, N.Y.), TAXOTERE (Aventis Pharmaceuticals, France), docetaxel, 10-desacetyl analogues of paclitaxel and 3'N-desbenzoyl-3'N-t-butoxy carbonyl analogues of paclitaxel. Paclitaxel has a molecular weight of about 853 amu, and may be readily prepared utilizing techniques known to those skilled in the art (see, e.g., Schiff et al., *Nature* 277: 665-667, 1979; Long and Fairchild, *Cancer Research* 54: 4355-4361, 1994; Ringel and Horwitz, *J. Nat'l Cancer Inst* 83 (4): 288-291, 1991; Pazdur et al., *Cancer Treat Rev.* 19 (4): 351-386, 1993; *Tetrahedron Letters* 35 (52): 9709-9712, 1994; *J. Med. Chem.* 35: 4230-4237, 1992; *J. Med. Chem.* 34: 992-998, 1991; *J. Natural Prod.* 57 (10): 1404-1410, 1994; *J. Natural Prod.* 57 (11): 1580-1583, 1994; *J. Am. Chem. Soc.* 110: 6558-6560, 1988), or obtained from a variety of commercial sources, including for example, Sigma Chemical Co., St. Louis, Mo. (T7402—from *Taxus brevifolia*).

Any single therapeutic agent or combination of therapeutic agents may be used in the medical device. Desirably, the therapeutic agent is paclitaxel or a derivative thereof. Paclitaxel may be used to prevent restenosis by preventing chronic inflammation (by preventing the division of affected cells by stabilizing the microtubule function) and by preventing cell migration (by preventing the cell with destructive potential from migrating and accumulating at the injured site).

Dose Levels of Therapeutic Agents

The therapeutically effective amount of therapeutic agent that is provided in connection with the various embodiments ultimately depends upon the condition and severity of the condition to be treated; the type and activity of the specific therapeutic agent employed; the method by which the medical device is administered to the patient; the age, body weight, general health, gender and diet of the patient; the time of administration, route of administration, and rate of excretion of the specific compound employed; the duration of the treatment; drugs used in combination or coincidental with the specific compound employed; and like factors well known in the medical arts.

Local administration of therapeutic agents may be more effective when carried out over an extended period of time, such as a time period at least matching the normal reaction time of the body to an angioplasty procedure. At the same time, it may be desirable to provide an initial high dose of the therapeutic agent over a preliminary period. For example, local administration of a therapeutic agent over a period of days or even months may be most effective in treating or inhibiting conditions such as restenosis.

For the purposes of local delivery from a stent, the daily dose that a patient will receive depends at least on the length of the stent. For example, a 15 mm long cylindrical radially expandable stent may contain a therapeutic agent in an amount ranging from about 1 μg to about 120 μg and may deliver that therapeutic agent over a time period ranging from several hours to several months, preferably up to about 1 to 6 months. Optionally, the medical device may be a stent adapted for placement in a peripheral, rather than coronary, artery (for instance, to treat peripheral vascular disease). To obtain the desired dosage of therapeutic agent, the thickness of the layer(s) may be varied, as well as the ratio of the zein/levulinic acid to the therapeutic agent. Preferably, the ratio of the weight of zein/levulinic acid to the therapeutic agent is about 1:1 to 20:1, more preferably about 5:1 to about 20:1, about 10:1 to about 20:1, about 15:1 to about 20:1 and most preferably about 17:1 to about 20:1, including ratios of 20, 19, 18, 17, 16, 15, 14, 13, 12, 11, 10, 9, 8, 7, 6, 5, 4, 3, 2 and 1 part zein/levulinic acid to 1 part of the therapeutic agent.

Therapeutic Agent Elution Profile

The therapeutic agent elution profile of a medical device comprising a therapeutic agent can be obtained by any suitable method that allows for measurement of the release of the therapeutic agent with a desired level of accuracy and precision. For purposes of this application, unless otherwise specified, the elution profile of the release of a therapeutic agent was obtained by contacting the medical device with a test solvent, such as a porcine serum or an aqueous cyclodextrin solution. A suitable test solvent solubilizes a therapeutic agent while allowing for subsequent measurement of the solubilized therapeutic agent in a manner that can be correlated to the amount of therapeutic agent released from the medical device. For example, porcine serum can be used to simulate implantation within a blood vessel.

The release of therapeutic agent from the medical device can be subsequently measured by any suitable spectrographic method, such as measurement of a UV absorption spectrum of an aqueous test solvent after contacting the medical device, or by use of an HPLC spectrophotometer with a UV-VIS detector, or a Liquid Chromatography paired with a Mass spec detector. A suitable method, such as a spectrographic technique, permits measurement of a property of the test solution that can be correlated to the presence or concentration of the therapeutic agent analyte with a desired level of accuracy and precision.

Figure 5:
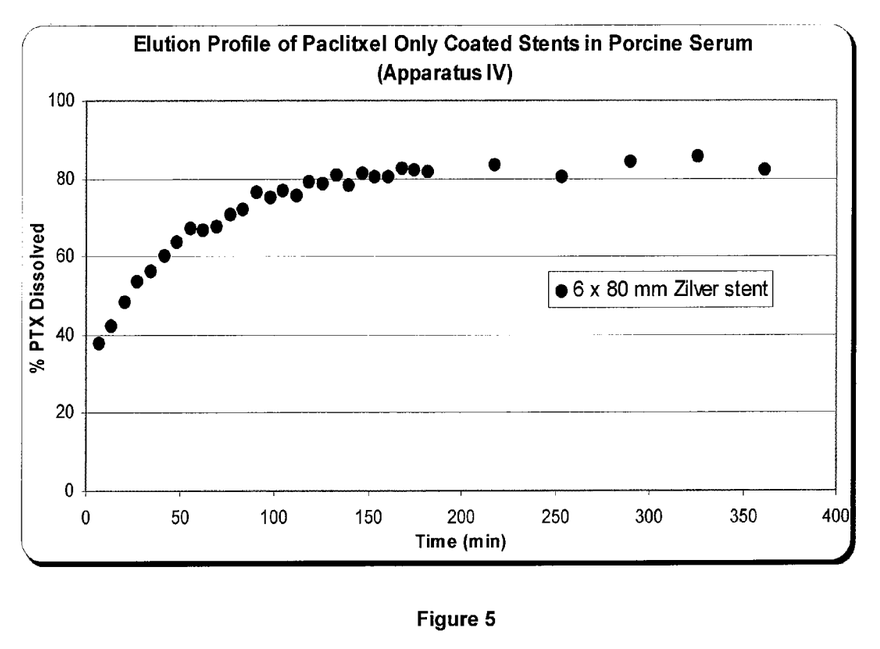
FIG. 5 shows the elution profile of a medical device coated with only paclitaxel

FIG. 5 shows a graph of a drug elution from a paclitaxel coated stent, without a zein/levulinic layer, in porcine serum. The elution graph shows the percent of 961 µg of paclitaxel eluted from a paclitaxel-coated 6×80 mm ZILVER stent in porcine serum as a function of time. The elution rate profile of the drug shows a high rate of drug delivery over an initial period of about 2 hours or so after stent contact with the porcine serum, with minimal drug eluted over the next several hours.

Elution profiles of stents coated with a layer of paclitaxel and a layer of zein/levulinic acid are shown in the examples below. Desirably, the medical device is configured to provide elution of therapeutic agent over at least about 3 to 6 months following introduction of the device into a physiological environment.

Figure 6:
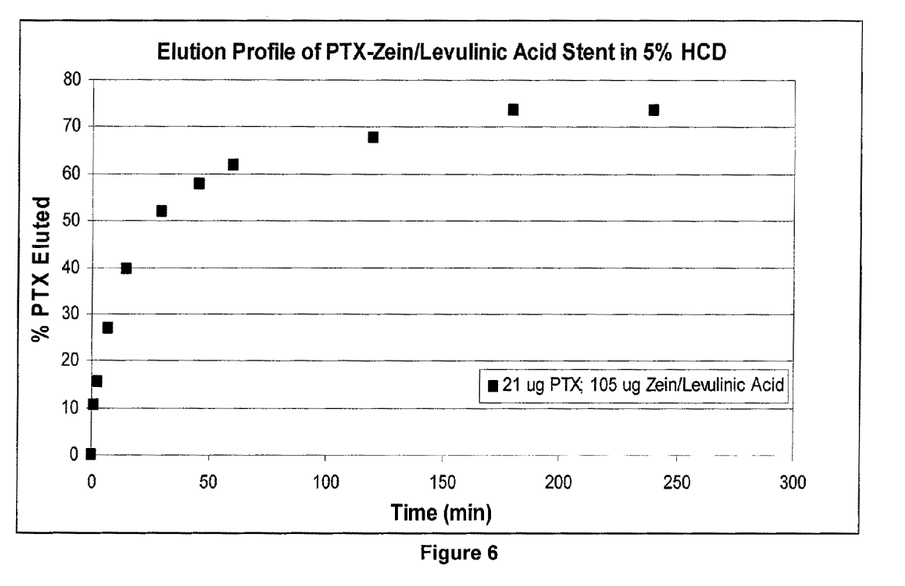
FIG. 6 shows an elution profile for one example in heptakis (2,6-dr-O-methyl)-β-cyclodextrin ("HCD").

Coating zein/levulinic over the paclitaxel-coated stent described with reference to FIG. 5 results in a notable change in the drug elution profile of paclitaxel. FIG. 6 shows a graph of drug elution in HCD from a sterilized paclitaxel-zein/levulinic coated stent, in accordance with one embodiment of the present disclosure. The elution graph shows the elution of paclitaxel from a sterilized paclitaxel-zein/levulinic coated stent in HCD. Elution media comprising HCD allows for rapid dissolution compared to porcine serum, used in FIG. 5. HCD was selected to provide desirably rapid therapeutic agent elution rates that remain dependent upon and indicative of the stent coating composition.

The stent is coated on the abluminal surface, with a first layer of paclitaxel and a second layer of zein positioned over the first layer. The elution of therapeutic agent is indicated as a percentage by weight of total drug initially deposited on the stent. Typical units for drug elution include micrograms of drug. The FIG. 6 zein/levulinic acid-coated stent elution rate profile shows a substantially slower in vivo rate of drug elution compared to the paclitaxel-only stent elution profile of FIG. 5, and was obtained from a stent coated only on the abluminal surface with 21 µg of paclitaxel in a first layer covered with 105 µg of zein/levulinic acid in a second layer. The zein/levulinic acid layer comprises 1 drop of levulinic per 10 mL of Methanolic zein solution (about 4 g/L).

Figure 7:
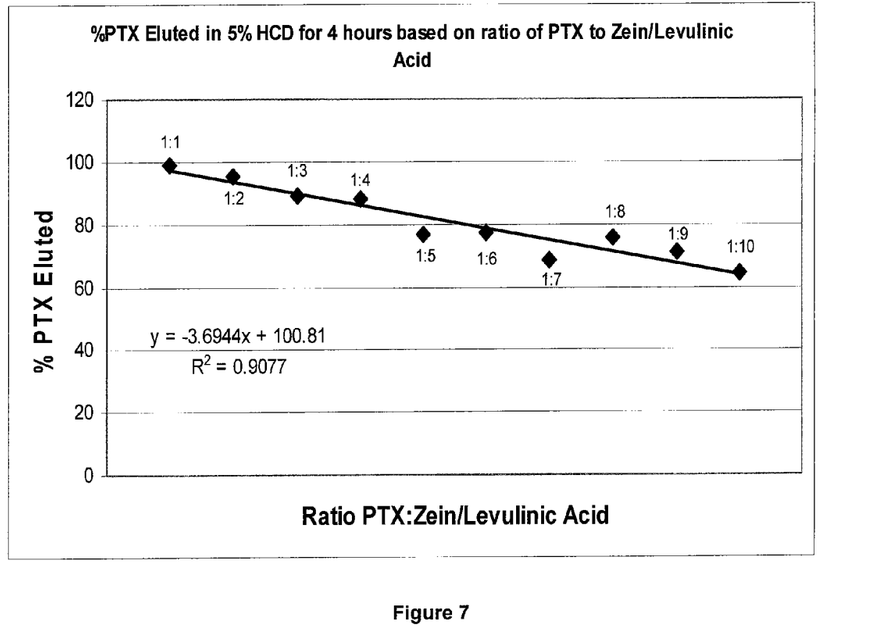
FIG. 7 shows the percent of paclitaxel eluted over four hours in an HCD solution as a function of the ratio of paclitaxel to zein admixed with levulinic acid.

FIG. 7 shows the percent of paclitaxel eluted over 4 hours in 5% HCD as a function of the ratio of paclitaxel to zein/levulinic acid. The correlation between the percent of paclitaxel eluted and the paclitaxel-zein/levulinic acid ration is a simple linear equation, illustrating that the elution of a therapeutic agent can be easily controlled by varying the amount of zein/levulinic acid. An increase in the ratio of zein/levulinic acid to paclitaxel yields a slower elution rate. A decrease in the ratio of zein/levulinic acid to paclitaxel generates a faster controlled elution rate.

Medical Devices

The present disclosure is applicable to implantable or insertable medical devices of any shape or configuration. Typical subjects (also referred to herein as "patients") are vertebrate subjects (i.e., members of the subphylum cordata), including, mammals such as cattle, sheep, pigs, goats, horses, dogs, cats and humans.

Typical sites for placement of the medical devices include the coronary and peripheral vasculature (collectively referred to herein as the vasculature), heart, esophagus, trachea, colon, gastrointestinal tract, biliary tract, urinary tract, bladder, prostate, brain and surgical sites. Where the medical device is inserted into the vasculature, for example, the therapeutic agent may be released to a blood vessel wall adjacent the device, and may also be released to downstream vascular tissue as well.

The medical device may be any device that is introduced temporarily or permanently into the body for the prophylaxis or therapy of a medical condition. For example, such medical devices may include, but are not limited to, stents, stent grafts, vascular grafts, catheters, guide wires, balloons, filters (e.g., vena cava filters), cerebral aneurysm filler coils, intraluminal paving systems, sutures, staples, anastomosis devices, vertebral disks, bone pins, suture anchors, hemostatic barriers, clamps, screws, plates, clips, slings, vascular implants, tissue adhesives and sealants, tissue scaffolds, myocardial plugs, pacemaker leads, valves (e.g., venous valves), abdominal aortic aneurysm (AAA) grafts, embolic coils, various types of dressings, bone substitutes, intraluminal devices, vascular supports, or other known bio-compatible devices.

In general, intraluminal stents for use in connection with the present disclosure typically comprise a plurality of apertures or open spaces between metallic filaments (including fibers and wires), segments or regions. Typical structures include: an open-mesh network comprising one or more knitted, woven or braided metallic filaments; an interconnected network of articulable segments; a coiled or helical structure comprising one or more metallic filaments; and, a patterned tubular metallic sheet (e.g., a laser cut tube). Examples of intraluminal stents include endovascular, biliary, tracheal, gastrointestinal, urethral, esophageal and coronary vascular stents. The intraluminal stents may be, for example, balloon-expandable or self-expandable. Thus, although certain embodiments will be described herein with reference to vascular stents, the present disclosure is applicable to other medical devices, including other types of stents.

In one embodiment, the medical device comprises an intraluminal stent. The stent may be self-expanding or balloon-expandable and may be a bifurcated stent, a stent configured for any blood vessel including coronary arteries and peripheral arteries (e.g., renal, Superficial Femoral, Carotid, and the like), a urethral stent, a biliary stent, a tracheal stent, a gastrointestinal stent, or an esophageal stent, for example. More specifically, the stent may be, for example, a Wallstent, Palmaz-Shatz, Wiktor, Strecker, Cordis, AVE Micro Stent, Igaki-Tamai, Millenium Stent (Sahajanand Medical Technologies), Steeplechaser stent (Johnson & Johnson), Cypher (Johnson & Johnson), Sonic (Johnson & Johnson), BX Velocity (Johnson & Johnson), Flexmaster (JOMED) JoStent (JOMED), S7 Driver (Medtronic), R-Stent (Orbus), Tecnic stent (Sorin Biomedica), BiodivYsio (Biocompatibles Cardiovascular), Trimaxx (Abbott), DuraFlex (Avantec Vascular), NIR stent (Boston Scientific), Express 2 stent (Boston Scientific), Liberte stent (Boston Scientific), Achieve (Cook/Guidant), S-Stent (Guidant), Vision (Guidant), Multi-Link Tetra (Guidant), Multi-Link Penta (Guidant), or Multi-Link Vision (Guidant). Some exemplary stents are also disclosed in U.S. Pat. No. 5,292,331 to Boneau, U.S. Pat No. 6,090,127 to Globerman, U.S. Pat No. 5,133,732 to Wiktor, U.S. Pat. No. 4,739,762 to Palmaz, and U.S. Pat. No. 5,421,955 to Lau. Desirably, the stent is a vascular stent such as the commercially available Gianturco-Roubin FLEX-STENT®, GRII™, SUPRA-G, or V FLEX coronary stents from Cook Inc. (Bloomington, Ind.).

The stent may be formed through various methods, such as welding, laser cutting, sputter deposition, or molding, or it may consist of filaments or fibers that are wound or braided together to form a continuous structure. The stent may also be a grafted stent in which the therapeutic agent is incorporated into the graft material. The stent may be deployed according to conventional methodology, such as by an inflatable balloon catheter, by a self-deployment mechanism (after release from a catheter), or by other appropriate means.

The stent or other medical device may be made of one or more suitable biocompatible materials such as stainless steel, nitinol, MP35N, gold, tantalum, platinum or platinum iridium, niobium, tungsten, iconel, ceramic, nickel, titanium, stainless steel/titanium composite, cobalt, chromium, cobalt/chromium alloys, magnesium, aluminum, or other biocompatible metals and/or composites or alloys such as carbon or carbon fiber, cellulose acetate, cellulose nitrate, silicone, cross-linked polyvinyl alcohol (PVA) hydrogel, cross-linked PVA hydrogel foam, polyurethane, polyamide, styrene isobutylene-styrene block copolymer (Kraton), polyethylene teraphthalate, polyurethane, polyamide, polyester, polyorthoester, polyanhydride, polyether sulfone, polycarbonate, polypropylene, high molecular weight polyethylene, polytetrafluoroethylene, or other biocompatible polymeric material, or mixture of copolymers thereof; polyesters such as, polylactic acid, polyglycolic acid or copolymers thereof, a polyanhydride, polycaprolactone, polyhydroxybutyrate valerate or other biodegradable polymer, or mixtures or copolymers thereof; extracellular matrix components, proteins, collagen, fibrin or other therapeutic agent, or mixtures thereof. Desirably, the device is made of stainless steel or nitinol.

Surface Preparation

It may be advantageous to prepare the surface of a medical device before depositing a coating thereon. Useful methods of surface preparation may include, but are not limited to: cleaning; physical modifications such as etching, drilling, cutting, or abrasion; chemical modifications such as solvent treatment; application of primer coatings or surfactants; plasma treatment; ion bombardment; and covalent bonding. Such surface preparation may activate the surface and promote the deposition or adhesion of the coating on the surface. Surface preparation may also selectively alter the release rate of the bioactive material. Any additional coating layers may similarly be processed to promote the deposition or adhesion of another layer, to further control the release rate of the therapeutic agent, or to otherwise improve the biocompatibility of the surface of the layers. For example, plasma treating an additional coating layer before depositing a therapeutic agent thereon may improve the adhesion of the therapeutic agent, increase the amount of therapeutic agent that can be deposited, and allow the bioactive material to be deposited in a more uniform layer.

A primer layer, or adhesion promotion layer, may be used with the medical device. This layer may include, for example, silane, acrylate polymer/copolymer, acrylate carboxyl and/or hydroxyl copolymer, polyvinylpyrrolidone/vinylacetate copolymer, olefin acrylic acid copolymer, ethylene acrylic acid copolymer, epoxy polymer, polyethylene glycol, polyethylene oxide, polyvinylpyridine copolymers, polyamide polymers/copolymers polyimide polymers/copolymers, ethylene vinylacetate copolymer and/or polyether sulfones.

Methods of Treatment

A method of treatment involves inserting into a patient a coated medical device having any of the configurations described above. For example, when the medical device is a stent coated as described above, the method of treatment involves implanting the stent into the vascular system of a patient and allowing the therapeutic agent(s) to be released from the stent in a controlled manner, as shown by the drug elution profile of the coated stent.

Although exemplary embodiments of the disclosure have been described with respect to the treatment of complications such as restenosis following an angioplasty procedure, the local delivery of therapeutic agents may be used to treat a wide variety of conditions using any number of medical devices. For example, other medical devices that often fail due to tissue ingrowth or accumulation of proteinaceous material in, on, or around the device may also benefit from the present disclosure. Such devices may include, but are not limited to, intraocular lenses, shunts for hydrocephalus, dialysis grafts, colostomy bag attachment devices, ear drainage tubes, leads for pace makers, and implantable defibrillators.

In one embodiment, a method of delivering a therapeutic agent to a body vessel, such as a peripheral blood vessel is provided. The method may include one or more of the following steps:

(a) providing a coated vascular stent comprising a radially-expandable vascular stent having an abluminal side and a luminal side defining a substantially cylindrical lumen and being movable from a radially expanded configuration to a radially compressed configuration; and a multi-layer coating on the abluminal surface.

(b) intralumenally inserting the coated vascular stent into the blood vascular system using a means for intralumenal delivery comprising a catheter;

(c) positioning the coated vascular stent within a peripheral artery; and (d) radially expanding the coated vascular stent within the peripheral artery so as to place the coated vascular stent in contact with a portion of a wall of the peripheral artery in a manner effective to deliver the therapeutic agent to the wall of the peripheral artery.

The multi-layer may include two or more layers, but typically includes a first layer comprising a therapeutic agent and a second layer comprising zein/levulinic acid positioned over the first layer and the first layer positioned between the surface and a second layer. The first layer preferably includes between about 0.05 and 2.00 μg, more preferably about 0.05 to 1.00 μg of a taxane therapeutic agent, such as paclitaxel, per $mm^2$ of the coated surface, and less than 0.1 μg of a polymer. The second layer preferably includes between about 0.05 and 40 μgrams of zein/levulinic acid per $mm^2$ of the coated surface, the total amount of zein/levulinic acid preferably being present in an amount between 1 and 20 times the weight of the therapeutic agent in the first layer.

A consensus document has been assembled by clinical, academic, and industrial investigators engaged in preclinical interventional device evaluation to set forth standards for evaluating drug-eluting stents such as those contemplated by the present disclosure. See "Drug-Eluting Stents in Preclinical Studies—Recommended Evaluation From a Consensus Group" by Schwartz and Edelman (Schwartz et al., Circulation 2002; 106:1867-1873, which is incorporated herein by reference).

While various aspects and examples have been described, it will be apparent to those of ordinary skill in the art that many more examples and implementations are possible within the scope of the disclosure. Accordingly, the disclosure is not to be restricted except in light of the attached claims and their equivalents.

EXAMPLES

Example 1

Single Layer of Zein/Levulinic Acid Over Single Layer of Paclitaxel on a Stent

Paclitaxel was applied to several 6×20 mm ZILVER stents (nitinol stents manufactured by Cook Inc.) as follows. First, paclitaxel was dissolved in ethanol to form a 2.4 mM solution. The paclitaxel was substantially dissolved within about 30 minutes, using sonication. The paclitaxel solution was then filtered through a 0.2 micron nylon filter and collected in a flask.

Approximately 10 mL+/−0.1 mL of ethanol was filtered through a 0.2 micron nylon filter and then transferred into a reservoir connected to a pressure spray gun nozzle. This solution was then used to set the flow rate of the pressure spray gun to the target flow rate of approximately 5.7 mL/min.+/−mL/min.

Some stents were mounted on a mandrel assembly positioned in the lumen of the stent, including a silicon tube covering a steel rod. This assembly masked the lumens of the stents and substantially prevented the lumens from being coated.

Approximately 25 mL of the filtered paclitaxel solution was added to the spray gun reservoir, and the solution was sprayed onto the stents using a HEPA filtered hood and a fluid dispensing system connected to a pressure source (nitrogen) until the target dose of paclitaxel was reached (for comparison, some stents were coated with more paclitaxel than others). Adjustments on the system were used to control the spray pattern and the amount of fluid dispensed. The spray gun was aligned with the stents by setting a laser beam even with the nozzle of the spray gun and positioning the stents so that the laser beam was located at approximately one quarter (¼) the distance from the top of the stents. The spray gun, which was positioned parallel to the hood floor and at a horizontal distance of approximately 12-18 centimeters from the stents, was then passed over the surface of the stents until a predetermined volume of spray was dispensed. The stents were then rotated approximately 90 degrees and the spraying procedure was repeated until the entire circumference of each stent was coated. The movement of the gun was slow enough to allow the solvent to evaporate before the next pass of the gun. Each spray application covered approximately 90 degrees of the circumference of the stents. The stents were kept at ambient temperature and humidity during the spraying process, and the solution was pumped at a rate of approximately 6 mL/min through the pressure spray gun. After substantially all of the solvent had evaporated, a coating of paclitaxel between about 0.07 μg mm$^{-2}$ and about 1.37 μg mm$^{-2}$ was left on the stent.

Zein was then applied over the paclitaxel coating. A solution of approximately 4 g/L of zein in methanol was prepared, filtered over a 0.2 micron nylon filter, and collected in a flask. The Methanolic solution of zein was then admixed with about 1 drop levulinic acid per 10 mLs of methanolic zein solution. The zein/levulinic acid solution was deposited over the layer of paclitaxel using an ultrasonic nozzle. The ultrasonic nozzle power was about 1.1 watts with a flow rate between 0.06 mL/min. and 0.08 mL/min. The nozzle was positioned at a horizontal distance of between approximately 11 mm and 15 mm from the stents. The zein/levulinic acid solution was coated on the stent at a velocity of about 25.5 mm/sec.

The coated stent was sterilized with ethylene oxide, and loaded into a flask containing HCD. Samples were taken at intervals and analyzed for paclitaxel. Numerical data for some of the resulting coated stents is shown in tables 3 and 4 below.

TABLE 3

| 21 μg PTX/21 μg Zein/Levulinic Acid | |
|---|---|
| Time (min) | % PTX Eluted |
| 0 | 0 |
| 1 | 1.7 |
| 3 | 7.1 |
| 7 | 12.8 |
| 15 | 23.5 |
| 30 | 44.3 |
| 45 | 53.6 |
| 60 | 58.9 |
| 120 | 65.2 |
| 180 | 67.3 |
| 240 | 67.9 |

TABLE 4

| 21 μg PTX/210 μg Zein/Levulinic Acid | |
|---|---|
| Time (min) | % PTX Eluted |
| 0 | 0 |
| 1 | 10.2 |
| 3 | 14.8 |
| 7 | 18.9 |
| 15 | 24.9 |
| 30 | 32.0 |
| 45 | 36.7 |
| 60 | 39.7 |
| 120 | 46.6 |
| 180 | 50.1 |
| 240 | 52.7 |

Example 2

Ultrasonic Coating of Multi-Layer Coating

Several multilayer coatings were applied to several 6×20 mm ZILVER stents (Cook Inc., Bloomington, Ind.). All coating layers were applied from a Sono-tek Model 8700-60 ultrasonic nozzle operated at parameters within Table 1 above. First, a solution of 0.7-4.8 mM paclitaxel in ethanol was sprayed onto the abluminal surface of each stent using the ultrasonic nozzle operated within the parameters provided in Table 1 above. Second, after application of the paclitaxel, a second solution of zein ~4 g/L in methanol was admixed with about 1 drop levulinic acid per 10 mL methanolic zein. The zein/levulinic acid solution was sprayed over the paclitaxel using the Sono-tek Model 8700-60 ultrasonic nozzle according to the parameters in Table 1.

Each solution was separately loaded into a 10.0 mL syringe, which was mounted onto a syringe pump and connected to a tube that carries the solution to a spray head. The syringe pump was then used to purge the air from the solution line and prime the line and spray nozzle with the solution. The ultrasonic nozzle is arranged such that excitation of the piezoelectric crystals generates a transverse standing wave along the length of the nozzle. The solution introduced onto the atomizing surface absorbs some of the vibrational energy, setting up wave motion in the liquid. By coating the solution according to the parameters in Table 1, the vibrational amplitude of the atomizing surface was adequate to provide a desired spray for application of the paclitaxel or zein/levulinic acid. The coating chamber is purged with nitrogen to displace any oxygen in the system. After that, the stent is loaded onto a mandrel and coated. The ultrasonic nozzle was manually aligned to the tip of each end of the stent. These position numbers are used for the coating program for when the syringe pump is actually activated. During the process, the stent is kept at ambient temperature and in a closed chamber.

We claim:

1. An expandable medical device comprising a frame and a coating, wherein the coating comprises from about 0.05 to about 40 µg of zein or modified zein admixed with levulinic acid per $mm^2$ of the coated surface of the medical device, wherein levulinic acid increases flexibility of the coating to accommodate deformations of the expandable medical device.

2. The device of claim 1, wherein the coating further comprises therapeutic agent.

3. The device of claim 2, wherein the therapeutic agent is hydrophobic.

4. The device of claim 2, wherein the coating further comprises about 1:1 to about 1:20 weight ratio of therapeutic agent to zein or modified zein admixed with levulinic acid.

5. The device of claim 2, wherein the coating further comprises about 1:1 to about 1:5 weight ratio of therapeutic agent to zein or modified zein admixed with levulinic acid.

6. The medical device of claim 1, wherein the coating further comprises at least two layers, a first layer comprising a therapeutic agent and a second layer comprising zein or modified zein admixed with levulinic acid.

7. The medical device of claim 6, wherein the second layer at least partially covers the first layer.

8. The device of claim 6, wherein the first layer is substantially covered by the second layer.

9. The device of claim 2, wherein the therapeutic agent is selected from the group consisting of anti-inflammatory/immunomodulators, antiproliferatives, migration inhibitors/ECM-modulators, and agents that promote healing.

10. The device of claim 9, wherein the therapeutic agent is paclitaxel or a paclitaxel derivative.

11. The device of claim 1, wherein the thickness of the coating on at least one point on the surface of the device is between about 0.2-10 microns.

12. The device of claim 1, wherein the medical device is selected from the group consisting of stents, stent grafts, vascular grafts, catheters, guide wires, balloons, filters, cerebral aneurysm filler coils, intraluminal paving systems, sutures, staples, anastomosis devices, vertebral disks, bone pins, suture anchors, hemostatic barriers, clamps, screws, plates, clips, slings, vascular implants, tissue adhesives and sealants, tissue scaffolds, myocardial plugs, pacemaker leads, valves, abdominal aortic aneurysm (AAA) grafts, embolic coils, various types of dressings, bone substitutes, intraluminal devices, and vascular supports.

13. The device of claim 1, wherein the frame is selected from the group consisting of stainless steel, nitinol, tantalum, a nonmagnetic nickel-cobalt-chromium-molybdenum [MP35N] alloy, platinum, titanium, a suitable biocompatible alloy, a suitable biocompatible material, and a combination thereof.

14. A medical device comprising a frame and a coating, the coating being the product of deposition of zein or modified zein solution comprising 1 to 3 drops of levulinic acid per 10 mL of the solution, and wherein from about 0.05 to about 40 µg of zein is present per $mm^2$ of the coated surface of the medical device, the coating comprising about 1:1 to about 1:20 weight ratio taxane therapeutic agent to zein or modified zein admixed with levulinic acid.

15. The device of claim 14, wherein the coating comprises about 0.01 to about 1.5 µg of taxane therapeutic agent per $mm^2$ of the frame.

16. The device of claim 14, wherein the coating comprises about 0.3 to about 1.0 µg of therapeutic agent per $mm^2$ of the frame.

17. The device of claim 14, wherein the medical device is selected from the group consisting of stents, stent grafts, vascular grafts, catheters, guide wires, balloons, filters, cerebral aneurysm filler coils, intraluminal paving systems, sutures, staples, anastomosis devices, vertebral disks, bone pins, suture anchors, hemostatic barriers, clamps, screws, plates, clips, slings, vascular implants, tissue adhesives and sealants, tissue scaffolds, myocardial plugs, pacemaker leads, valves, abdominal aortic aneurysm (AAA) grafts, embolic coils, various types of dressings, bone substitutes, intraluminal devices, and vascular supports.

18. The device of claim 14, wherein the medical device is a vascular stent.

19. The device of claim 14, wherein the therapeutic agent is paclitaxel or a paclitaxel derivative.

20. A method of delivering a therapeutic agent to a patient in need thereof comprising the steps of
providing an expandable medical device and
implanting the medical device in a patient wherein the medical device comprises
at least one therapeutic agent and
a coating comprising from about 0.05 to about 40 µg of zein admixed with levulinic acid per $mm^2$ of the coated surface of the medical device with a ratio of about 1:1 to about 1:20 by weight of the at least one therapeutic agent to zein admixed with levulinic acid, and wherein levulinic acid increases flexibility of the coating to accommodate deformations of the expandable medical device during the implanting step.

* * * * *